US012788706B2

(12) United States Patent
Florence et al.

(10) Patent No.: US 12,788,706 B2
(45) **Date of Patent: *Nov. 10, 2026**

(54) MULTI-PURPOSE COSMETIC COMPOSITIONS

(71) Applicant: MARY KAY INC., Addison, TX (US)

(72) Inventors: Tiffany Florence, Dallas, TX (US); Michelle Hines, Hickory Creek, TX (US); David Gan, Southlake, TX (US)

(73) Assignee: MARY KAY INC., Addison, TX (US)

( * ) Notice: Subject to any disclaimer, the term of this patent is extended or adjusted under 35 U.S.C. 154(b) by 501 days.

This patent is subject to a terminal disclaimer.

(21) Appl. No.: 18/512,630

(22) Filed: Nov. 17, 2023

(65) Prior Publication Data

US 2024/0277602 A1 Aug. 22, 2024

Related U.S. Application Data

(60) Continuation of application No. 17/076,612, filed on Oct. 21, 2020, now Pat. No. 11,857,667, which is a continuation of application No. 16/146,273, filed on Sep. 28, 2018, now Pat. No. 10,842,733, which is a continuation of application No. 15/073,300, filed on Mar. 17, 2016, now Pat. No. 10,188,595, which is a continuation of application No. 14/333,376, filed on Jul. 16, 2014, now Pat. No. 9,320,702, which is a division of application No. 13/341,616, filed on Dec. 30, 2011, now Pat. No. 8,815,308.

(60) Provisional application No. 61/428,740, filed on Dec. 30, 2010.

(51) Int. Cl.

| | |
|---|---|
| ***A61K 8/9711*** | (2017.01) |
| ***A61K 8/9789*** | (2017.01) |
| ***A61K 36/28*** | (2006.01) |
| ***A61K 36/287*** | (2006.01) |
| ***A61K 36/42*** | (2006.01) |
| ***A61Q 17/04*** | (2006.01) |
| ***A61Q 19/00*** | (2006.01) |
| ***A61Q 19/08*** | (2006.01) |
| *A61Q 1/02* | (2006.01) |
| *A61Q 19/10* | (2006.01) |

(52) U.S. Cl.

CPC .......... *A61K 8/9711* (2017.08); *A61K 8/9789* (2017.08); *A61K 36/28* (2013.01); *A61K 36/287* (2013.01); *A61K 36/42* (2013.01); *A61Q 19/00* (2013.01); *A61Q 19/008* (2013.01); *A61Q 19/08* (2013.01); *A61K 2800/10* (2013.01); *A61K 2800/5922* (2013.01); *A61Q 1/02* (2013.01); *A61Q 17/04* (2013.01); *A61Q 19/004* (2013.01); *A61Q 19/10* (2013.01); *Y02A 50/30* (2018.01)

(58) Field of Classification Search

CPC .... A61K 8/9711; A61K 8/9789; A61K 36/28; A61K 36/287; A61K 36/42; A61K 2800/10; A61K 2800/5922; A61K 2800/782; A61K 8/97; A61K 36/02; A61K 36/03; A61K 36/24; A61K 36/55; A61K 36/61; A61K 36/62; A61K 8/04; A61K 2300/00; A61Q 19/00; A61Q 19/008; A61Q 19/08; A61Q 1/02; A61Q 17/04; A61Q 19/004; A61Q 19/10; A61Q 19/007; Y02A 50/30; A61P 17/00; A61P 17/08; A61P 17/18

See application file for complete search history.

(56) References Cited

U.S. PATENT DOCUMENTS

| | | | |
|---|---|---|---|
| 4,211,577 | A | 7/1980 | Wallin |
| 4,302,200 | A | 11/1981 | Yokoyama et al. |
| 4,409,254 | A | 10/1983 | Garin et al. |
| 4,749,573 | A | 6/1988 | Bonne et al. |
| 4,996,196 | A | 2/1991 | Mitsuhashi et al. |
| 5,089,410 | A | 2/1992 | Murata et al. |
| 5,560,916 | A | 10/1996 | Koulbanis et al. |
| 5,595,756 | A | 1/1997 | Bally |
| 5,804,168 | A | 9/1998 | Murad |
| 5,942,231 | A | 8/1999 | Hamada et al. |
| 6,159,484 | A | 12/2000 | Kilian et al. |
| 6,217,913 | B1 | 4/2001 | Mohammadi |
| 6,296,859 | B1 | 10/2001 | Stolz |
| 6,468,564 | B1 | 10/2002 | Riley et al. |
| 6,524,599 | B2 | 2/2003 | Pinnell |
| 6,623,745 | B2 | 9/2003 | Borgnine |

(Continued)

FOREIGN PATENT DOCUMENTS

| | | |
|---|---|---|
| CA | 1334006 | 1/1995 |
| CN | 1843325 | 10/2006 |

(Continued)

OTHER PUBLICATIONS

"Monarda Didyma Leaf Extract," *International Cosmetics Ingredient Dictionary and Handbook*, 12th *edition*, Gottschalck and Bailey, Ed., *The Cosmetic, Toiletry and Fragrance Association*, Washington, D.C., 2:1605, 2008.

"Natural Botanical Extract" Carrubba 1-247, 2007, URL:http://www.carrubba.com/pdf/Carrubba_Botanical_Guide_r.pdf.

"Simmondsia Chinensis (Jojoba) Leaf Extract," *International Cosmetics Ingredient Dictionary and Handbook*, 12th *edition*, Gottschalck and Bailey, Ed., *The Cosmetic, Toiletry and Fragrance Association*, Washington, D.C., 2:2478-2479, 2008.

(Continued)

*Primary Examiner* — Aaron J Kosar

(74) *Attorney, Agent, or Firm* — NORTON ROSE FULBRIGHT US LLP

(57) ABSTRACT

A method for treating the skin of a subject in need thereof is disclosed. The method includes topically applying to the skin of the subject a cosmetic composition that includes an effective amount of an aqueous, alcoholic, or aqueous-alcoholic extract of *Silybum marianum* and an aqueous, alcoholic, or aqueous-alcoholic extract of *Momordica grosvenori* fruit.

19 Claims, No Drawings

(56) References Cited

U.S. PATENT DOCUMENTS

| | | | | |
|---|---|---|---|---|
| 6,649,178 | B2 | 11/2003 | Mohammadi et al. | |
| 6,680,062 | B2 | 1/2004 | Muizzuddin et al. | |
| 6,783,754 | B2 | 8/2004 | Mankovitz | |
| 6,905,696 | B2 | 6/2005 | Marotta et al. | |
| 7,399,783 | B2 | 7/2008 | Rosenbloom | |
| 7,563,779 | B2 | 7/2009 | Henderson et al. | |
| 7,575,764 | B2 | 8/2009 | Chen et al. | |
| 7,722,904 | B2 | 5/2010 | Schneider et al. | |
| 8,815,308 | B2 * | 8/2014 | Florence | A61K 36/28 424/725 |
| 8,828,455 | B2 | 9/2014 | Florence | |
| 8,877,259 | B2 | 11/2014 | Florence | |
| 9,320,702 | B2 | 4/2016 | Florence et al. | |
| 9,358,203 | B2 | 6/2016 | Florence et al. | |
| 10,188,595 | B2 | 1/2019 | Florence et al. | |
| 10,588,851 | B2 * | 3/2020 | Florence | A61K 8/60 |
| 11,857,667 | B2 * | 1/2024 | Florence | A61K 2300/00 |
| 2001/0014351 | A1 | 8/2001 | Wang | |
| 2002/0155074 | A1 | 10/2002 | Pinnel | |
| 2005/0142095 | A1 | 6/2005 | Scancarella et al. | |
| 2006/0134095 | A1 | 6/2006 | Ito et al. | |
| 2006/0147397 | A1 | 7/2006 | Uehara et al. | |
| 2006/0233738 | A1 | 10/2006 | Miyata et al. | |
| 2008/0033037 | A1 | 2/2008 | Bernard et al. | |
| 2009/0041866 | A1 | 2/2009 | Miyata et al. | |
| 2009/0246163 | A1 | 10/2009 | Wahi | |
| 2009/0285917 | A1 | 11/2009 | Jeong et al. | |
| 2009/0325885 | A1 | 12/2009 | Miyata et al. | |
| 2010/0021571 | A1 | 1/2010 | Waugh et al. | |
| 2010/0233128 | A1 | 9/2010 | Panasenko | |
| 2010/0247563 | A1 | 9/2010 | Hines et al. | |

FOREIGN PATENT DOCUMENTS

| | | |
|---|---|---|
| CN | 101129311 | 2/2008 |
| CN | 101141946 | 3/2008 |
| JP | 2243613 | 9/1990 |
| JP | 10130137 | 5/1998 |
| KR | 19970039403 | 8/1997 |
| KR | 1999012076 | 2/1999 |
| KR | 19990016741 | 3/1999 |
| KR | 100773856 | 11/2007 |
| KR | 20080138117 | 12/2008 |
| KR | 2010056239 | 5/2010 |
| KR | 20100079586 | 7/2010 |
| WO | WO 2006/063402 | 6/2006 |
| WO | WO 2006/087569 | 8/2006 |
| WO | WO 2007/105864 | 9/2007 |

OTHER PUBLICATIONS

Anonymous: "Nymphea gigantean flower extract" Ingredients of Cosmetics Jun. 9, 2010, URL:http://ingredientsofcosmetics.com/ingredient/nymphaea%20gigantea%20flower%20extract.

Anonymous: "Plumeria alba flower extract" Ingredients of Cosmetics Oct. 7, 2009, URL:http://ingredientsofcosmetics.com/ingredient/plumeria%20alba%20flower%20extract.

Begoun, Paula, and Bryan Barron. Don't Go to the Cosmetics Counter Without Me. Renton, Wash.: Beginning Press, 2008. pp. 1128-1129.

Carruba Inc, "Natural Botanical Extracts," publication, [retrieved from Internet on Dec. 21, 2017], published 226 Feb. 2001, <URL: https://web.archive.org/web/20101225101318/http://www.carrubba.com/pdf/Carrubba_Botanical_Guide_r.pdf > 247 pp.

Chabner et al. Perspectives: Chemotherapy and the War on Cancer; Nature Review. Cancer 5.1 (Jan. 2005):65-72.

Fang et al., "High Quality Cultivation Techniques of Traditional Chinese Medicine in Nanyang," Sanqin Publishing House, 2004, p. 524.

Guan et al. *China Ocean Plants: Marine Medicinal Microorganism*. 1st ed., Shanghai Scientific & Technical Publishers, 2009, p. 34.

Guan et al., "Chinese Marine Herbal, vol. 3, Marine Invertebrate Medicine," Shanghai Scientific & Technical Publishers, 2009, p. 53.

Guan, H. Section 3 Marine invertebrates drug, China Ocean Plants. Shanghai Science and Technology Press, p. 53. 2009.

International Search Report and Written Opinion issued in PCT Application No. PCT/US2011/068190, dated Aug. 30, 2012.

Li, B. Marin Health Food. Chemical Industry Press, pp. 110-114. 2009.

Li, Bafang. The active composition of marine organisms. China Ocean University Press, 2007, p. 177-180.

Morvan, P-Y, et al. "Stem cell approach 'makes aged skin young' Personal Care Mar. 1, 2009, pp. 49-52, URL:" http://www.codif-recherche-et-nature.com/userfiles/PUBLICATIONS/StemcellsPersonalCareEuropeMrch2009013.pdf.

Newton et al., "Medicinal Chemistry," Shanghai Scientific and Technical Literature Publishing House, 2008, pp. 26-27.

Newton, D. E. et al. Medicinal Chemistry. Shanghai Scientific and Technical Literature Publishing House, p. 26-27. 2008.

Office Action and Search Report issued in Chinese Patent Application No. 201610594152.8, dated Aug. 3, 2018.

Office Action issued in Chinese Application No. 201180066354.0, dated Jul. 17, 2014.

Office Action issued in Corresponding Chinese Application No. 2017110646875, dated Apr. 2, 2021 (English Translation provided).

Pompeu et al., "Optimisation of the solvent extraction of phenolic antioxidants from fruits of *Euterpe oleracea* using Response Surface Methodology," *Bioresource Technology*, 2009, 100:6076-6082.

Search Report issued in Corresponding Chinese Application No. 2017110646875, dated Mar. 9, 2021 (English Translation provided).

Supplementary European Search Report issued on Dec. 3, 2014.

Tang, Mingchuan. Skincare advice-facial care. Shanghai Jiao Tong University Press, 2009, pp. 108-110.

Tassone et al. Novel Therapeutic Approaches Based on the Targeting of Microenvironemnt-Derived Survival Pathways in Human Cancer: Experimental Models and Translational Issues; Current Pharmaceutical Design 13.5 (Feb. 2007) 487-496.

Wang et al., "Cosmetic Plant Materials Encyclopaedia," China Textile Press, 2012, pp. 406-407.

Wang et al., "Cosmetic Plant Materials Encyclopaedia," China Textile Press, 2012, pp. 348-349.

Wang, Benxiang. Pharmacology of Modern Chinese Medicine. Tianjin Science and Technology Press, 1997, p. 976.

Wang, J. Manual of Plant Materials used in Cosmetics. Chemical Industry Press, pp. 9-10, 110-111. 2006.

Wang, Jianxin "Natural active cosmetics," China Light Industry Press, 1997, p. 225.

Wu et al., Female common disease prevention and healthcare. Central University for Nationalities Pres, 1995, p. 321.

Wyatt et al., "Phytochemical Analysis and Biological Screening of Leaf and Twig Extracts from *Kunzea ericoides*," *Phytotherapy Research*, 2005, 19:963-970.

Youwei et al., "A comparative study on the free radical scavenging activities of some fresh flowers in southern China," *LWT—Food Science and Technology*, 2008, 41:1586-1591.

Zhu et al., "Cosmetic Botany," China Agricultural University Press, 2009, p. 68.

* cited by examiner

MULTI-PURPOSE COSMETIC COMPOSITIONS

CROSS REFERENCE TO RELATED APPLICATIONS

This application is a continuation of U.S. patent application Ser. No. 17/076,612 filed Oct. 21, 2020, which is a continuation of U.S. patent application Ser. No. 16/146,273 filed Sep. 28, 2018 (now U.S. Pat. No. 10,842,733), which is a continuation of U.S. patent application Ser. No. 15/073,300 filed Mar. 17, 2016 (now U.S. Pat. No. 10,188,595), which is a continuation of U.S. patent application Ser. No. 14/333,376 filed Jul. 16, 2014 (now U.S. Pat. No. 9,320,702), which is a divisional of U.S. patent application Ser. No. 13/341,616 filed Dec. 30, 2011 (now U.S. Pat. No. 8,815,308), which claims the benefit of U.S. Provisional Application 61/428,740 filed Dec. 30, 2010. The contents of the referenced applications are incorporated into the present application by reference.

BACKGROUND OF THE INVENTION

A. Field of the Invention

The present invention relates generally to multi-purpose topical skin compositions that can be used on dry skin, oily skin, normal skin, or combination skin.

B. Description of Related Art

There are thousands of skin formulations available to consumers. Further, there are a myriad of different skin types among the population. Such skin types range from normal skin, dry skin, oily skin, and combination skin (e.g., normal/dry, normal/oily, dry/oily). The leads to a confusing and exhaustive search for different products for different applications.

SUMMARY OF THE INVENTION

The inventor found a solution to the aforementioned problems. This solution is premised on the use of particular combination of ingredients that synergistically work on all skin-types ranging from normal skin, dry skin, oily skin and combination skin (e.g., normal/dry, normal/oily, dry/oily). In this regard, two separate combinations of natural ingredients were identified and confirmed to be effective across all skin types. Further, the inventor identified subcombinations of natural ingredients that can be specifically tailored for a given skin-type.

In one instance, for example, the combination of *Silybum marianum* extract and *Momordica grosvenori* fruit extract (primary combination) was found to be effective on all skin-types of normal, dry, and oily skin. The addition of *Linum usitatissimum* seed extract and hydrolyzed algin to the primary combination was found to work well on dry skin. The addition of *Psidium guajava* fruit extract and *Kunzea ericoides* leaf extract to the primary combination was found to work well on oily skin. The addition of

*Plumeria alba* flower extract and *Nymphea gigantea* flower extract to the primary combination was found to work well on normal skin.

In another instance, for example, the combination of *Silybum marianum* extract and *Pseudopterogorgia elisabethae* extract (primary combination) was found to be effective on all skin-types of normal, dry, and oily skin. The addition of *Linum usitatissimum* seed extract and hydrolyzed algin to the primary combination was found to work well on dry skin. The addition of *Psidium guajava* fruit extract and *Spiraea ulmaria* extract to the primary combination was found to work well on oily skin. *Psidium guajava* fruit extract was a hydroglycolic fruit extract. The addition of *Plumeria alba* flower extract, *Euterpe oleraceae* fruit extract, and *Camellia sinensis* leaf extract to the primary combination was found to work well on normal skin. The *Plumeria alba* flower extract was an aqueous extract.

In one instance, the formulations described in Tables 11-19 can be used as vehicles for any of the combinations of the present invention. Such formulations are generic and can be modified by increasing or decreasing the amount of the various ingredients, which explains why ranges are provided. In particular embodiments, the water can by increased or decreased as needed. Further, although the claims section do not identify the specific formulations in Tables 11-19, it is intended by the inventors that such claims may be made. Therefore, Tables 11-19 are incorporated into the summary of the invention section by reference.

In one aspect, there is disclosed a method for treating skin comprising topically applying to skin in need thereof a composition that includes an effective amount of *Silybum marianum* extract and *Momordica grosvenori* fruit extract, wherein topical application of the composition treats the skin, wherein the *Silybum marianum* extract can be a hydroalcoholic extract and the *Momordica grosvenori* fruit extract can be a hydroglycolic extract. An effective amount can be 0.01 to 5% by weight of *Silybum marianum* extract and 0.01 to 5% by weight of *Momordica grosvenori* fruit extract. The composition can have anti-oxidative properties that can reduce oxidative damage to skin cells. The composition can be a cream, lotion, gel, serum, or an emulsion (e.g., an oil-in-water emulsion or a water-in-oil emulsion). The composition can be alcohol-free or substantially alcohol-free. Examples of alcohols include ethanol, methanol, denatured alcohol, propanol, and other alcohols know to those of ordinary skill in the art (e.g., compounds having —OH groups). In instances where the skin is determined to be dry skin, the composition can further include an effective amount of *Linum usitatissimum* seed extract and hydrolyzed algin, wherein the *Linum usitatissimum* seed extract can be a hydroglycolic extract and wherein the hydrolyzed algin can be obtained from *Laminaria digitata* or can be an aqueous solution of an oligosaccharide produced by controlled enzymatic depolymerization of membranous polysaccharides from *Laminaria digitata*. The oligosaccharide can be a chain of 2 uronic acids, mannuronic and guluronic, illustrated by the following structure:

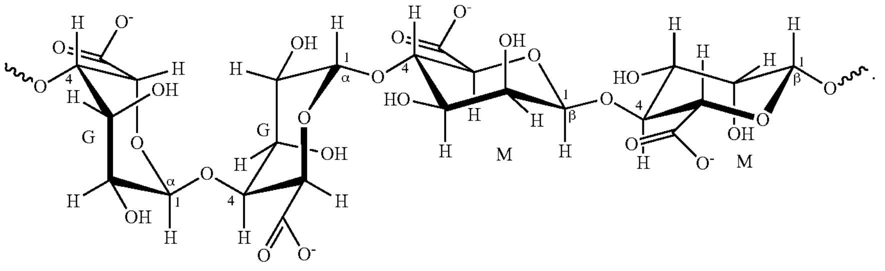

An effective amount can be 0.01 to 5% by weight of *Silybum marianum* extract, 0.01 to 5% by weight of *Momordica grosvenori* fruit extract, 0.01 to 5% by weight of *Linum usitatissimum* seed extract, and 0.01 to 5% by weight of hydrolyzed algin. The composition can reduce in skin cells any one of or all of or any combination of the following: CGRP expression; Cyclo-oxygenase 1 and 2 activity; FAAH activity; lipoxygenase activity; TNF-α expression; IL-2, 8, and 10 activity; angiogenin expression; INF-γ expression; IL 12p40 expression; and/or tyrosinase activity. In instances wherein the skin is determined to be oily skin, the composition can further include an effective amount of *Psidium guajava* fruit extract and *Kunzea ericoides* leaf extract, wherein the *Psidium guajava* fruit extract is a hydroglycolic fruit extract and wherein the *Kunzea ericoides* leaf extract is an aqueous extract. An effective amount can be 0.01 to 5% by weight of *Silybum marianum* extract, 0.01 to 5% by weight of *Momordica grosvenori* fruit extract, 0.01 to 5% by weight of *Psidium guajava* fruit extract, and 0.01 to 5% by weight of *Kunzea ericoides* leaf extract. The composition can reduce sebum production in sebaceous glands. In instances wherein the skin is determined to be normal skin, the composition can further include an effective amount of *Plumeria alba* flower extract and *Nymphea gigantea* flower extract, wherein the *Plumeria alba* flower extract is an aqueous extract, and wherein the *Nymphea gigantea* flower extract is an aqueous extract. An effective amount can be 0.01 to 5% by weight of *Silybum marianum* extract, 0.01 to 5% by weight of *Momordica grosvenori* fruit extract, 0.01 to 5% by weight of *Plumeria alba* flower extract, and 0.01 to 5% by weight of *Nymphea gigantea* flower extract.

Also disclosed is a method for treating skin comprising topically applying to skin in need thereof a composition that includes an effective amount of *Silybum marianum* extract and either one of or both of *Momordica grosvenori* fruit extract or *Pseudopterogorgia elisabethae* extract, wherein a hydroglycolic extract, and the *Pseudopterogorgia elisabethae* extract. The *Pseudopterogorgia elisabethae* extract can be a butylene glycol, caprylic/capric triglyceride, or pentylene glycol extract that includes pseudopterosins. The composition can include *Silybum marianum* extract and *Momordica grosvenori* fruit extract or *Silybum marianum* extract and *Pseudopterogorgia elisabethae* extract or *Silybum marianum* extract, *Momordica grosvenori* fruit extract, and *Pseudopterogorgia elisabethae* extract. The composition can have anti-oxidative properties that can reduce oxidative damage to skin cells. The composition can be a cream, lotion, gel, serum, or emulsion (e.g., an oil-in-water emulsion or a water-in-oil emulsion). The composition can be alcohol-free or substantially alcohol-free. Examples of alcohols include ethanol, methanol, denatured alcohol, propanol, and other alcohols know to those of ordinary skill in the art (e.g., compounds having —OH groups). The composition can further include *Helianthus annuus* seed extract. The *Helianthus annuus* seed extract can be an aqueous extract, oil extract, or alcohol extract. The composition can reduce in skin cells any one of or all of or any combination of the following: CGRP expression; Cyclo-oxygenase 1 and 2 activity; FAAH activity; lipoxygenase activity; TNF-α expression; IL-2, 8, and 10 activity; angiogenin expression; INF-γ expression; IL 12p40 expression; and/or tyrosinase activity. In instances where the skin is determined to be dry skin, the composition can further include an effective amount of *Linum usitatissimum* seed extract and hydrolyzed algin, wherein the *Linum usitatissimum* seed extract can be a hydroglycolic extract and wherein the hydrolyzed algin can be obtained from *Laminaria digitata* or can be an aqueous solution of an oligosaccharide produced by controlled enzymatic depolymerization of membranous polysaccharides from *Laminaria digitata*. The oligosaccharide can be a chain of 2 uronic acids, mannuronic and guluronic, illustrated by the following structure:

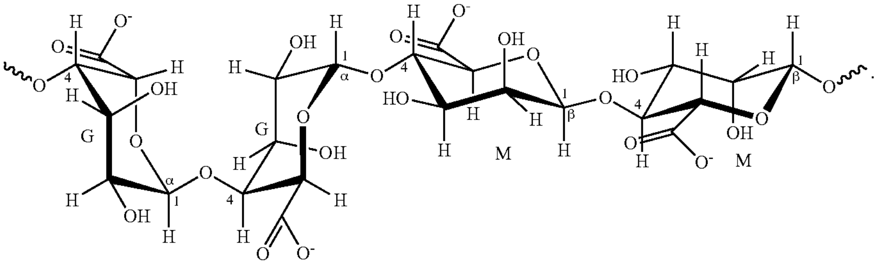

topical application of the composition treats the skin, wherein the *Silybum marianum* extract can be a hydroalcoholic extract, the *Momordica grosvenori* fruit extract can be In instances where the skin is determined to be oily skin, the composition can further include an effective amount of *Psidium guajava* fruit extract and either one of or both of

*Kunzea ericoides* leaf extract or *Spiraea ulmaria* extract, wherein the *Psidium guajava* fruit extract can be a hydroglycolic fruit extract and the *Kunzea ericoides* leaf extract can be an aqueous extract. The *Spirea ulmaria* extract can be an aqueous or alcoholic extract. The composition can reduce sebum production in sebaceous glands. In instances wherein the skin is determined to be normal skin, the composition can include an effective amount of *Plumeria alba* flower extract and either of or all of *Nymphea gigantea* flower extract, *Euterpe oleraceae* fruit extract, and/or *Camellia sinensis* leaf extract, wherein the *Plumeria alba* flower extract can be an aqueous extract and the *Nymphea gigantea* flower extract can be an aqueous extract. The *Euterpe oleraceae* fruit extract can be an aqueous or alcoholic extract, and/or *Camellia sinensis* leaf extract can be an aqueous or alcoholic extract. An effective amount of each extract can be 0.01 to 5% by weight of the composition.

In other aspects there is disclosed multi-purpose compositions that can have multiple ingredients. The ingredients can include *Silybum marianum* extract, luo han guo fruit extract, guava fruit extract, gorgonian extract, flax seed extract, hydrolyzed algin, frangipani flower extract, *Nymphaea gigantea* flower extract, and kanuka leaf extract. In particular, the combination of *Silybum marianum* extract and luo han guo fruit extract can be used to provide anti-aging benefits to skin (e.g., treat wrinkles and aged spots), reduce skin irritation and symptoms associated with erythema (e.g., red skin), and reduce or treat itchy skin by removing or reducing the itchy feeling that can lead to scratching skin. Another combination found to be effective is *Silybum marianum* extract, luo han guo fruit extract, and gorgonian extract. The inventors also discovered that the combination of *Silybum marianum* extract, luo han guo fruit extract, flax seed extract, and hydrolyzed algin had a wide range of skin efficacy effects. A further combination that also produced positive skin efficacy results was *Silybum marianum* extract, luo han guo fruit extract, frangipani flower extract, and *Nymphaea gigantea* flower extract. Yet another combination of ingredients found to have a wide range of skin efficacy effects was *Silybum marianum* extract, luo han guo fruit extract, guava fruit extract, and kanuka leaf extract. Additional combinations that also proved to be effective in treating skin conditions was flax seed extract combined with hydrolyzed algin, frangipani extract combined with water lily extract, and guava fruit extract combined with kanuka extract.

In one embodiment there is disclosed a method for treating or preventing a skin condition comprising topically applying a composition that includes an effective amount of *Silybum marianum* extract and *Momordica grosvenori* fruit extract to skin in need thereof, wherein topical application of the composition treats or prevents the skin condition. The *Silybum marianum* extract can be a hydroalcoholic extract that includes silymarin. The *Momordica grosvenori* fruit extract can be a hydroglycolic extract. The effective amount of any one of the extracts individually or in combination can be 0.01 to 5% by weight (or more such as 6, 7, 8, 9, 10, 20, 30, 40, 50%). The composition can reduce in skin cells any one of or all of or any combination of the following: CGRP expression; Cyclo-oxygenase 1 and 2 activity; FAAH activity; lipoxygenase activity; TNF-α expression; IL-2, 8, and 10 activity; angiogenin expression; INF-γ expression; IL 12p40 expression; and/or tyrosinase activity. The composition can have anti-oxidatative properties that can reduce oxidative damage to skin cells. The composition can increase ICAM-1 expression in skin cells. The composition can be a cream, lotion, gel, serum, anhydrous base, oil-in-water emulsion, a water-in-oil emulsion, etc.

The composition can include a combination of *Silybum marianum* extract, *Momordica grosvenori* fruit extract, and an extract derived from *Pseudopterogorgia elisabethae*. The extract derived from *Pseudopterogorgia elisabethae* can be a butylenes glycol, caprylic/capric triglyceride, or pentylene glycol extract that includes pseudopterosins. The effective amount of this combination of extract can be individually or in combination 0.01 to 5% by weight (or more such as 6, 7, 8, 9, 10, 20, 30, 40, 50%). This combination can reduce in skin cells any one of or all of or any combination of the following: CGRP expression; Cyclo-oxygenase 1 and 2 activity; FAAH activity; lipoxygenase activity; TNF-α expression; IL-2, 8, and 10 activity; angiogenin expression; INF-γ expression; IL 12p40 expression; and/or tyrosinase activity. This combination can have anti-oxidative properties that can reduce oxidative damage to skin cells. This combination can also increase ICAM-1 expression in skin cells.

The composition can include a combination of *Silybum marianum* extract, *Momordica grosvenori* fruit extract, *Linum usitatissimum* seed extract, and hydrolyzed algin. The *Linum usitatissimum* seed extract can be is a hydroglycolic extract. The hydrolyzed algin can be obtained from *Laminaria digitata* and/or is an aqueous solution of an oligosaccharide produced by controlled enzymatic depolymerization of membranous polysaccharides from *Laminaria digitata*. The oligosaccharide can be a chain of 2 uronic acids, mannuronic and guluronic, illustrated by the following structure:

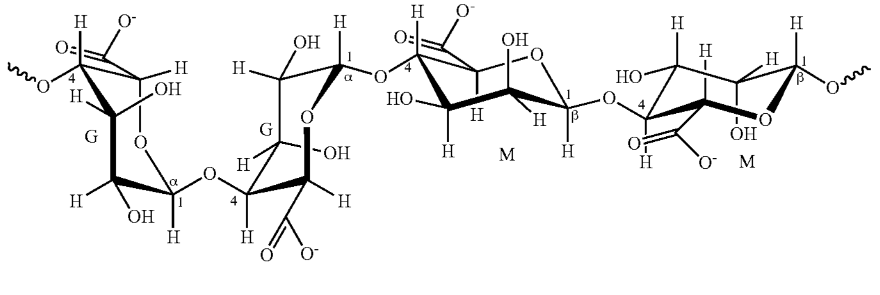

The effective amount of this combination of extract can be individually or in combination 0.01 to 5% by weight (or more such as 6, 7, 8, 9, 10, 20, 30, 40, 50%). This combination can reduce in skin cells any one of or all of or any combination of the following: CGRP expression; Cyclo-oxygenase 1 and 2 activity; FAAH activity; lipoxygenase activity; TNF-α expression; IL-2, 6, 8, and 10 expression; angiogenin expression; INF-γ expression; IL 12p40 expression; tyrosinase activity; MMP2, 3, and 9 activity; and/or melanogenesis activity. This combination can have anti-oxidative properties that can reduce oxidative damage to skin cells. This combination can increase laminin expression and ICAM-1 expression in skin cells. This combination can be used as an involucrin reporter.

The composition can include a combination of *Silybum marianum* extract, *Momordica grosvenori* fruit extract, *Plumeria alba* flower extract, and *Nymphea gigantea* flower extract. The *Plumeria alba* flower extract can be an aqueous extract. The *Nymphea gigantea* flower extract can be an aqueous extract. The effective amount of this combination of extract can be individually or in combination 0.01 to 5% by weight (or more such as 6, 7, 8, 9, 10, 20, 30, 40, 50%). This combination can reduce in skin cells any one of or all of or any combination of the following: CGRP expression; Cyclo-oxygenase 1 and 2 activity; FAAH activity; lipoxygenase activity; TNF-α expression; IL-2, 6, 8, and 10 expression; angiogenin expression; INF-γ expression; IL 12p40 expression; tyrosinase activity; MMP2, 3, and 9 activity; and/or melanogenesis activity. This combination can have anti-oxidative properties that can reduce oxidative damage to skin cells. This combination can increase laminin and ICAM-1 expression and collagen production in skin cells. This combination can be used as an involucrin reporter.

The composition can include a combination of *Silybum marianum* extract, *Momordica grosvenori* fruit extract, *Psidium guajava* fruit extract, and *Kunzea ericoides* leaf extract. The *Psidium guajava* fruit extract can be a hydro-glycolic fruit extract. The *Kunzea ericoides* leaf extract can be an aqueous extract. The effective amount of this combination of extract can be individually or in combination 0.01 to 5% by weight (or more such as 6, 7, 8, 9, 10, 20, 30, 40, 50%). This combination can reduce in skin cells any one of or all of or any combination of the following: CGRP expression; Cyclo-oxygenase 1 and 2 activity; FAAH activity; lipoxygenase activity; TNF-α expression; IL-2, 8, and 10 expression; angiogenin expression; INF-γ expression; IL 12p40 expression; tyrosinase activity; and/or elastase activity. This combination can have anti-oxidative properties that can reduce oxidative damage to skin cells. This combination can increase ICAM-1 expression and collagen production in skin cells.

Also disclosed is a method of treating or preventing a skin condition comprising topically applying a composition that includes an effective amount of *Linum usitatissimum* seed extract and hydrolyzed algin to skin in need thereof, wherein topical application of the composition treats or prevents the skin condition. The *Linum usitatissimum* seed extract can be a hydroglycolic extract. The hydrolyzed algin can be obtained from *Laminaria digitata* and/or is an aqueous solution of an oligosaccharide produced by controlled enzymatic depolymerization of membranous polysaccharides from *Laminaria digitata*. The oligosaccharide can be a chain of 2 uronic acids, mannuronic and guluronic, illustrated by the following structure:

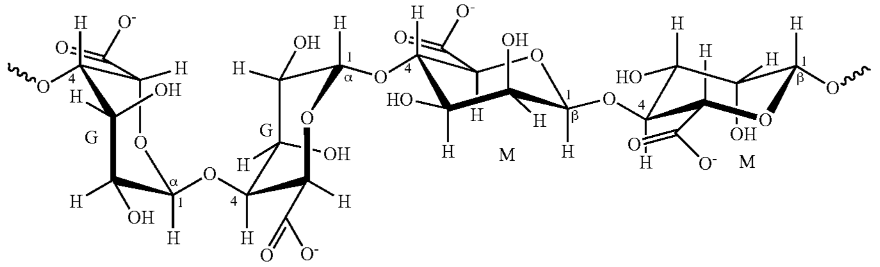

The effective amount of this combination of extract can be individually or in combination 0.01 to 5% by weight (or more such as 6, 7, 8, 9, 10, 20, 30, 40, 50%). This combination of extracts can reduce in skin cells any one of or all of or any combination of the following: MMP 2, 3, and 9 activity; CGRP expression; TNF-α expression; IL 6, 8, and 10 expression; IL12p40 expression, and/or melanogenesis activity. This combination can increase laminin production in skin cells and/or be used as an involucrin reporter. The composition can be a cream, lotion, gel, serum, and anhydrous base, an oil-in-water emulsion or a water-in-oil emulsion.

In another embodiment there is disclosed a method for treating or preventing a skin condition comprising topically applying a composition that includes an effective amount of *Plumeria alba* flower extract and *Nymphea gigantea* flower extract to skin in need thereof, wherein topical application of the composition treats or prevents the skin condition. The *Plumeria alba* flower extract can be an aqueous extract. The *Nymphea gigantea* flower extract can be an aqueous extract. The effective amount of this combination of extract can be individually or in combination 0.01 to 5% by weight (or more such as 6, 7, 8, 9, 10, 20, 30, 40, 50%). This combination of extracts can reduce in skin cells TNF-α expression. This combination can have anti-oxidative properties that can reduce oxidative damage to skin cells. This combination can increase collagen production in skin cells. The composition can be a cream, lotion, gel, serum, and anhydrous base, an oil-in-water emulsion or a water-in-oil emulsion.

In still another embodiment there is disclosed a method for treating or preventing a skin condition comprising topically applying a composition that includes an effective amount of *Psidium guajava* fruit extract and *Kunzea ericoides* leaf extract to skin in need thereof, wherein topical application of the composition treats or prevents the skin condition. The *Psidium guajava* fruit extract can be a hydroglycolic fruit extract. The *Kunzea ericoides* leaf extract can be an aqueous extract. The effective amount of this combination of extract can be individually or in combination 0.01 to 5% by weight (or more such as 6, 7, 8, 9, 10, 20, 30, 40, 50%). This combination of extracts can reduce in skin cells TNF-α expression and/or elastase activity. This combination can have anti-oxidative properties that can reduce oxidative damage to skin cells. This combination can increase collagen production in skin cells. The composition can be a cream, lotion, gel, serum, and anhydrous base, an oil-in-water emulsion or a water-in-oil emulsion.

The skin condition that can be treated with any one of the methods and/or compositions of the present can be: dry skin, flaky skin, itchy skin, chapped skin, pruritus, spider veins, lentigo, age spots, senile purpura, keratosis, melasma, blotches, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, sun burns, burned skin, open wounds, and/or skin-inflammatory skin conditions.

In one particular aspect there is disclosed a method of treating or preventing a fine line or wrinkle comprising topically applying to skin in need thereof any one of the compositions of the present invention, wherein topical application of said composition to a fine line or wrinkle treats said fine line or wrinkle.

In yet another embodiment there is disclosed a method of treating or preventing erythemic skin or symptoms associated with erythemic skin (e.g., red skin, flushed skin, etc.) comprising topically applying to skin in need thereof any one of the compositions of the present invention, wherein topical application of said composition to erythemic skin treats said erythemic skin. Erythema can be caused by skin irritation, an inflammatory response, skin sunburn, electrical treatments of skin, skin burns, contact allergies, systemic allergies, skin toxicity, exercise, insect stings, bacterial infection, viral infection, fungal infection, protozoa infection, massage, windburn, and other factors that can cause reddening or flushing of the skin etc. The compositions disclosed above and throughout this specification can be used. The compositions can also be used to reducing pain associated with erythema, sensitive skin, or inflamed skin, comprising topically applying to erythemic, sensitive, or inflamed skin a composition comprising jaboticaba fruit pulp and/or cashew fruit pulp or extracts thereof.

Also disclosed is a method of tightening or toning skin comprising topically applying to skin in need thereof a composition comprising any one of the compositions of the present invention, wherein topical application of said composition to skin tightens or tones said skin. The compositions disclosed above and throughout this specification can be used.

In even a further embodiment there is disclosed an ingestible composition comprising any one of the extracts or combinations of extracts disclosed throughout this specification and an ingestible acceptable vehicle. In certain aspects, the ingestible composition can be a food-based product, a pill, a gel capsule, a powder, or a neutraceutical product.

An additional embodiment includes an injectible solution comprising any one of the extracts or combinations of extracts disclosed throughout this specification and an ingestible acceptable vehicle and an injectibly acceptable solution. Injectibly acceptable solution includes a solution that can be safely injected into a human or animal.

One embodiment concerns a method of treating or preventing a disease comprising administering to a person in need thereof any one of the extracts or combinations of extracts disclosed throughout this specification, wherein the disease is treated or prevented. Non-limiting examples of diseases include AIDS, an autoimmune disease (e.g., rheumatoid arthritis, multiple sclerosis, diabetes-insulin-dependent and non-independent, systemic lupus erythematosus, or Graves disease), a cancer (e.g., malignant, benign, metastatic, or precancer), a cardiovascular disease (e.g., heart disease, or coronary artery disease, stroke-ischemic and hemorrhagic, or rheumatic heart disease), diseases of the nervous system, an infection by a pathogenic microorganism (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, or Viral hepatitis), inflammation (e.g., allergy, or asthma), a prion disease (e.g., CJD, kuru, GSS, or FFI), or obesity.

A further embodiment includes a method of treating or preventing hair loss comprising administering to a patient in need thereof a composition comprising any one of the compositions or any one of the extracts or combinations of extracts disclosed throughout this specification. The composition can be included a pharmaceutically (whether topical, oral, injectible, etc.) or dermatologically acceptable vehicle, wherein administering to the patient in need thereof prevents or treats hair loss. Preventing or treating hair loss can include stimulating hair growth on the scalp, in eyebrows, in eyelashes, or on other regions of the body where hair growth is desired. The composition can take the form of an edible pill or gel cap or liquid or powder or foam or spray or aerosolized. The composition can be topically applied, ingested, injected, etc.

The compositions of the present invention can take the form of a pill, gel capsule, spray, foam, topical cream, ointment, gel, or lotion, be aerosolized, or be in powdered form. The compositions can be formulated as emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (e.g., aqueous or hydro-alcoholic solutions), anhydrous bases (e.g., lipstick or a powder), gels, ointments, milks, pastes, aerosols, solid forms, eye jellies, etc. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). The compositions of the present invention can include any desired amount of jaboticaba or cashew extract or both. The amount of the extracts can individually or combined be from 0.001, 0.01, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 6, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, or more (or any range or integer therein), by weight or volume of the extract or combination of extracts. The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben. Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

In other aspects, any one of the compositions of the present invention can exclude/not have certain ingredients. By way of example, the compositions can exclude one of, two of, or all of *Hypsizygus ulmarius* ethanolic extract, *Ganoderma Lucidum* extract or *Cordyceps sinensis* extract. The compositions can exclude S-adenosylmethionine. The compositions, in certain aspects, is not applied to a scar or scar tissue. The composition can exclude soybean protein and/or tocopherol or alpha tocopherol. The composition can exclude an anti-inflammatory component and/or an immunity boosting component. The composition can exclude a peptide or a peptide having the amino acid sequence Gly-Pro-Hyp. The composition can be designed to not stimulate skin pigmentation. The composition can exclude a flavonoid or a flavonoid that is effective at reducing scar tissue or improving the appearance of scare tissue. The composition can exclude a cyanin derived from a plant (e.g., an anthocyanin and/or a betacyanin). The composition can be formulated to not be a sunscreen composition and to not have an effective SPF value to block UVA, UVB, and/or UVC radiation. The composition can exclude aloe vera gel, sea parsley extract, red clover extract, kava kava extract, bittersweet extract, sea pine extract, edelweiss extract and/or watercress extract. The composition can exclude an organic sun screen agent with a chromophoric group active within the ultraviolet radiation range from about 290 nm to about 400 nm. The composition can exclude a silicone fluid or hydrocarbon for retaining moisture within the skin, and/or does not include a $C_6$ to $C_{40}$ carboxylic ester. The composition can exclude guava leaves or an extract from guava leaves. The composition can exclude green tea, hiokitiol, phytosphingosine and/or a salicylate. The composition can exclude a flax glycerol-glycol-water biocomplex and/or a sucrose acetate isobutyrate. The composition can exclude a cationic agent having a cationic strength sufficient to fully neutralize any negative electrostatic charge on the skin, and/or extract of the seed of plant material selected from the group consisting of the Yellow Lotus (*Nelumbo lutea*), the Blue Lotus (*Nelumbo caerulea*) and the Sacred Lotus (*Nelumbo nucifera*). The composition can exclude kanuka oil and/or Chia seed (*Salvia hispanica*) oil.

Also disclosed is a method of lightening skin or evening skin tone comprising applying the compositions of the present invention to the skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, a freckle, a sun spot, hyper-pigmented skin, etc., by topical application of the composition to the age spot, a skin discoloration, a freckle, a sun spot, hyper-pigmented skin, etc.

Also disclosed is a method of treating hyperpigmentation comprising applying the compositions of the present invention to the skin. The method can also comprise identifying a person in need of treating hyperpigmentation and applying the composition to a portion of the skin exhibiting hyperpigmentation. Additional methods contemplated by the inventors include methods for reducing the appearance of an age spot, a skin discoloration, or a freckle, reducing or preventing the appearance of fine lines or wrinkles in skin, or increasing the firmness of skin by applying the compositions of the present invention to skin in need of such treatment.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, an anti-aging product, a deodorant, an antiperspirant, a perfume, a cologne, etc.

It is also contemplated that compositions of the present invention can be included into food-based products (e.g., beverages, fortified water, energy drinks, nutritional drinks, solid foods, vitamins, supplements, etc.) and pharmaceutical products (e.g., pills, injectible solutions, drugs, etc.). "Supplements" can include vitamins, minerals, herbs or other botanicals, amino acids, enzymes and metabolites. Such supplements are suitable for oral consumption and can be administered orally.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

The compositions and methods for their use can "comprise," "consist essentially of," or "consist of" any of the ingredients disclosed throughout the specification. For purposes of consisting essentially of means that inclusion of additional ingredients in the compositions do not materially affect the multi-beneficial properties of the aforementioned combination of ingredients. One such instance would be the inclusion of an ingredient that has a detrimental effect (e.g., reducing the efficacy or stability) on any one of the ingredients identified in the combination.

"Acne" includes pimples, black heads, white heads, papules, nodules, pustules, inflammatory lesions, or cysts.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or "treating" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Given the number of various products on the market today and the myriad of different skin-types, a person is oftentimes at a loss to identify an appropriate product. Further, many current products include caustic agents that can irritate skin, leave the skin feeling dry, or leave the skin feeling oily.

The inventors discovered a solution to counteract these issues. In particular, the solution concerns two separate combinations of ingredients obtained from natural sources that have been shown (see examples) to work on different skin types ranging from oily skin, dry skin, or normal skin. Further, subcombinations were found to work particularly well on a given skin type.

These and other non-limiting aspects of the present invention are described in further detail below.

A. Determining Skin-Type

A first step it utilizing the compositions of the present invention can be to determine a user's skin type. It is well known in the cosmetic's field that there are three main skin types: (1) normal skin; (2) dry skin; and (3) oily skin. A fourth skin type is simply a combination of any one of normal, dry, or oily skin (e.g., normal/dry, normal/oily, oily/dry). There are also well-known methods for determining a person's skin type.

For instance, normal skin can be identified as having a smooth texture and no greasy patches or flaky areas. Therefore, a product that can retain skin moisture in its present form can be used to maintain the appearance of normal skin.

As for dry skin, it has a low level of sebum production from sebaceous glands and is prone to irritation or erythema. The appearance of dry skin has a parched look caused by the skin's inability to retain moisture. Oftentimes it feels "tight" and uncomfortable after washing and is prone to chapping, flaking, and cracking. Dry skin can be exacerbated by wind, extremes of temperature and air-conditioning, all of which cause the skin to flake, chap and feel tight. Dry skin typically has a dull appearance. Therefore, a product that deliver appropriate hydration and restore moisture to dry skin can be used to counteract the effects of dry skin.

With respect to oily skin, such skin is shiny, thick and dull colored. It feels oily and has coarse pores and pimples and other unsightly blemishes due to overproduction of sebum from sebaceous glands and from clogged/blocked pores. In this regard, oily skin usually has oil producing sebaceous glands that are overactive and produce more oil than is needed. The oil oozes and gives the skin a greasy shine. The pores are enlarged and the skin has a coarse look. Therefore, a product that can help control skin surface oiliness while also cleansing clogged pores can be used to counteract the effects of oily skin.

As noted above, combination skin is a combination of both oily, dry, and/or normal skin (e.g., normal/dry, oily/dry, normal/oily). For oily/dry skin, there is typically a greasy center panel consisting of nose, forehead and chin (also known as the "T-zone" of a person's face) and a dry panel consisting of cheeks, mouth and the areas around the eyes. Therefore, a product that can control the excess oil production in sebaceous glands in the T-zone while also hydrating the dry skin areas outside of the T-zone can be used for such oily/dry skin.

Once a particular skin-type is identified, a person can then select an appropriate composition to correct or maintain the skin-type.

B. Combination of *Silybum marianum* and Luo Han Guo Fruit Extracts

The inventors discovered that the combination of *Silybum marianum* extract and *Momordica grosvenori* fruit extract was found to be effective on all skin-types of normal, dry, and oily skin.

Milk thistle (*Silybum marianum*) is a plant native to Southern Europe and Asia. It is known for producing red to purple flowers, shiny pale green leaves with white veins, and fruit. The *Silybum marianum* extract of the present invention is a hydroalcoholic (water and alcohol denat) extract that includes silymarin as an active ingredient (silymarin is a mixture of flavanonol derivatives that includes silibine, silicristine, silidianin, isosolibine, and isosilicristine). The fruit portion of *Silybum marianum* includes silymarin. The *Silybum marianum* extract can be obtained from the fruit portion of this plant by mascerating the fruit pulp and then subjecting the pulp to a hydroalcoholic solution of water and SD alcohol 39-C (alcohol denat.) to obtain the extract. The extract can then filtered and packaged for storage or be added to a composition of the present invention. In addition to this extraction process, *Silybum marianum* extract can be purchased from Provital S.A (SPAIN) under the trade names PRONALEN SILYMARIN HSC or PRONALEN SILYMARIN SPE.

Luo han guo (*Momordica grosvenori*) is a perennial vine that grows 3-5 meters long with narrow heart shaped leaves and green round fruit 5-7 cm in diameter. This plant is native to southern China. The fruit has been used as a natural food sweetener in China for several decades. The luo han guo extract of the present invention can be obtained from the fruit portion of this plant by macerating the fruit pulp and then subjecting the pulp to a hydroglycolic solution of water, glycerin, and preservatives to obtain the extract. The extract can then filtered and packaged for storage or be added to a composition of the present invention. In addition to this extraction process, luo han guo fruit extract can be purchased from Carrubba Inc., Milford, Connecticut (USA).

Data also suggests that the combination of these ingredients in a topical skin formulation can be used to treat a wide variety of skin conditions by reducing in skin cells the following: CGRP expression; Cyclo-oxygenase 1 and 2 activity; FAAH activity; lipoxygenase activity; TNF-α expression; IL-2, 8, and 10 activity; angiogenin expression; INF-γ expression; IL 12p40 expression; and tyrosinase activity. This combination also has anti-oxidative properties, which can be used to prevent or at the very least reduce oxidative damage to skin cells. This combination also can increase ICAM-1 expression in skin cells. Example 2 provides a more detailed account of these data.

1. Dry Skin

The addition of *Linum usitatissimum* seed extract and hydrolyzed algin to the *Silybum marianum* and luo han guo fruit extracts was found to work well on dry skin.

Flax seed (*Linum usitatissimum* (Linseed)) is an annual, biennial or perennial herb that can reach 3 feet in height. It includes a slender stem, lance-shaped leaves, and can produce ski-blue flowers and oily brown seeds. This plant is native to Europe and Asia. The flax seed extract of the present invention can be obtained from the seed portion of this plant by macerating the seed and then subjecting the seed to a hydroglycolic solution of water and glycerin to obtain the extract. The extract can then filtered and packaged for storage or be added to a composition of the present invention. In addition to this extraction process, flax seed extract can be purchased from Carrubba Inc., Milford, Connecticut (USA).

Hydrolyzed algin can be obtained from *Laminaria digitata*, which is a brown alga, that is found in the littoral zone of bodies of water. The hydrolyzed algin is an aqueous solution of an oligosaccharide that can be produced by controlled enzymatic depolymerization of membranous polysaccharides from *Laminaria digitata*. The structure of the oligosaccharide is a chain of 2 uronic acids: mannuronic and guluronic, which can be illustrated as follows:

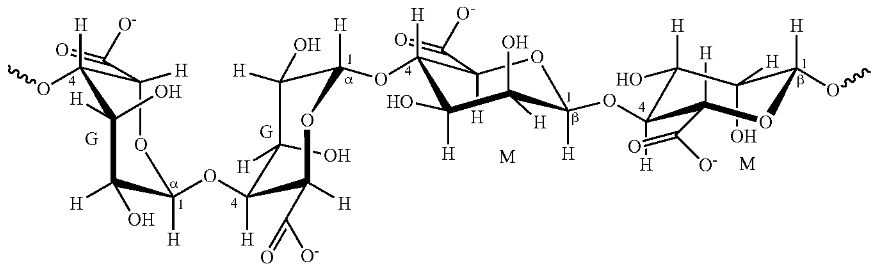

In addition to this production process, hydrolyzed algin can be purchased from Barnet Products Corp., Englewood Cliffs, New Jersey (USA) under the trade name PHYKO AL-PF.

Data also suggests that the combination of these ingredients in a topical skin formulation can be used to treat a wide variety of skin conditions by reducing in skin cells the following: CGRP expression; Cyclo-oxygenase 1 and 2 activity; FAAH activity; lipoxygenase activity; TNF-α expression; IL-2, 6, 8, and 10 expression; angiogenin expression; INF-γ expression; IL 12p40 expression; tyrosinase activity; MMP2, 3, and 9 activity; and melanogenesis activity. This combination also has anti-oxidative properties, which can be used to prevent or at the very least reduce oxidative damage to skin cells. This combination also has the ability to increase laminin expression and ICAM-1 expression in skin cells and can also be used as an involucrin reporter. Example 2 provides a more detailed account of these data.

2. Oily Skin

The addition of *Psidium guajava* fruit extract and *Kunzea ericoides* leaf extract to *Silybum marianum* and luo han guo fruit extracts was found to work well on oily skin.

Guava or *Psidium guajava* is an evergreen tree or shrub that can reach 6 to 25 feet in height. It produces green leaves, fragrant white flowers, and fruit. The fruit is pear-shaped and 3 to 6 cm in length. When ripe, the skin of the fruit has a reddish-yellow color. This plant is native to the region spanning Mexico to northern South America. The fruit portion of guava is used in the context of the present invention to obtain the extract. The guava fruit extract of the present invention can be produced by macerating the fruit pulp and then subjecting the pulp to a hydroglycolic solution of water and glycerin to obtain the extract. The extract can then be filtered and packaged for storage. In addition to this extraction process, guava fruit extract of the present invention can be purchased from Carrubba Inc., Milford, Connecticut (USA).

Kanuka or *Kunzea ericoides* is a tree that can reach up to 30 meters in height. The leaves have an oval shape and the flowers are white. This plant is native to Australia and New Zealand. The *Kunzea ericoides* leaf extract of the present invention can be obtained from the leaf portion of this plant by macerating the leaf and then subjecting the leaf to an aqueous extraction process. The extract can then be filtered, placed in a butylene glycol solution, and packaged for storage or be added to a composition of the present invention. In addition to this extraction process, kanuka leaf extract can be purchased from Southern Cross Botanicals, New South Wales (AUSTRALIA) under the trade name ABACROSS KANUKA BG.

Data also suggests that the combination of these ingredients in a topical skin formulation can be used to treat a wide variety of skin conditions by reducing in skin cells the following: CGRP expression; Cyclo-oxygenase 1 and 2 activity; FAAH activity; lipoxygenase activity; TNF-α expression; IL-2, 8, and 10 expression; angiogenin expression; INF-γ expression; IL 12p40 expression; tyrosinase activity; and elastase activity. This combination also has anti-oxidative properties, which can be used to prevent or at the very least reduce oxidative damage to skin cells. Further, this combination also has the ability to increase ICAM-1 expression and collagen production in skin cells. Example 2 provides a more detailed account of these data.

3. Normal Skin

The addition of *Plumeria alba* flower extract and *Nymphea gigantea* flower extract to *Silybum marianum* and luo han guo fruit extracts was found to work well on normal skin.

*Plumeria alba* (Frangipani) is a large evergreen shrub with narrow elongated leaves and large white followers that have a yellow center. It is native to Central America and the Caribbean. The frangipani flower extract of the present invention can be obtained from the flower portion of this plant by macerating the flower and then subjecting the flower to an aqueous extraction process. The extract can then be filtered, placed in a butylene glycol solution, and packaged for storage or be added to a composition of the present invention. In addition to this extraction process, frangipani flower extract can be purchased from Southern Cross Botanicals, New South Wales (AUSTRALIA) under the trade name ABACROSS FRANGIPANI FLOWER BG.

*Nymphea gigantea* (Giant Water Lily) is a tropical plant that is native to the tropical and subtropical regions of Australia. This plant can produce large (up to 25 cm) blue-white flowers that emerge from the water and large circular leaves that grow up to 75 cm in diameter. The *Nymphea gigantea* flower extract of the present invention can be obtained from the flower portion of this plant by macerating the flower and then subjecting the flower to an aqueous extraction process. The extract can then be filtered, placed in a butylene glycol solution, and packaged for storage or be added to a composition of the present invention. In addition to this extraction process, frangipani flower extract can be purchased from Southern Cross Botanicals, New South Wales (AUSTRALIA) under the trade name ABACROSS WATER LILY BG.

Data also suggests that the combination of these ingredients in a topical skin formulation can be used to treat a wide variety of skin conditions by reducing in skin cells the following: CGRP expression; Cyclo-oxygenase 1 and 2 activity; FAAH activity; lipoxygenase activity; TNF-α expression; IL-2, 6, 8, and 10 expression; angiogenin expression; INF-γ expression; IL 12p40 expression; tyrosinase activity; MMP2, 3, and 9 activity; and melanogenesis activity. This combination also has anti-oxidative properties, which can be used to prevent or at the very least reduce oxidative damage to skin cells. This combination also has the ability to increase laminin and ICAM-1 expression and collagen production in skin cells and can also be used as an involucrin reporter. Example 2 provides a more detailed account of these data.

C. Combination of *Silybum marianum* and Gorgonian Extracts

The inventors discovered that the combination of *Silybum marianum* extract and *Pseudopterogorgia elisabethae* extract was found to be effective on all skin-types of normal, dry, and oily skin.

*Silybum marianum* extract is described above.

Gorgonian extract is a marine extract derived from *Pseudopterogorgia elisabethae* (or Sea Whip) plant. *Pseudopterogorgia elisabethae* can be harvested from the Atlantic Ocean. Gorgonian extract can be prepared by macerating the *Pseudopterogorgia elisabethae* plant and then subjecting the macerated plant with butylenes glycol, or caprylic/capric triglyceride, or pentylene glycol. One of the active ingredients in Gorgonian extract can be pseudopterosins (e.g., pseudopterosin A). In addition to this extraction process, Gorgonian extract can be purchased from Lipo Chemicals Inc., Paterson, New Jersey (USA) under the trade names GORGONIAN EXTRACT BG, GORGONIAN EXTRACT GC, or GORGONIAN PTG.

In some instances, this combination can also include *Helianthus annus* (sunflower) seed extract. The sunflower is a plant that produces bright yellow sunflowers. Seeds are contained within the flower. It is native to North and South America. Sunflower seed extract is the extract of the seeds of the sunflower, can be purchased from Silab (France) under the trade names ANTIGLYSKIN™, ASPERILIKE 2™, BIOHAIR™, MX023-COMMUCELL™ GLYCALINE™, HELIOXINE™, MX016 SENSIKIN™, or RETICALMINE™

1. Dry Skin

The addition of *Linum usitatissimum* seed extract and hydrolyzed algin to the *Silybum marianum* and gorgonian extracts was found to work well on dry skin. Both of these extracts are described above.

2. Oily Skin

The addition of *Psidium guajava* fruit extract and *Spiraea ulmaria* extract to the *Silybum marianum* and gorgonian extracts was found to work well on oily skin. *Psidium guajava* fruit extract is described above.

*Spiraea ulmaria* (Meadow Sweet) is a perennial herb that is native throughout most of Europe and Western Asia. Extracts obtained from the leaf can be purchased from Gattefosse (Canada) under the trade name CYTOBIO ULMAIRE™. *Spiraea ulmaria* extract obtained from the whole plant can be purchased from Active Concepts (USA) under the trade name ACB MEADOWSWEET EXTRACT™, ACB MEADOWSWEET EXTRACT 20%™, from Silab (France) under the trade names DERMAPUR™, SEBONORMINE™, and SEBOREGUL™, or from Phytocos (France) under the trade names COMPLEXE AMINCISSANT LP1™ COMPLEXE AMINCISSANT SGLP™, EXTRAIT d'ULMAIRE LP1™, and EXTRAIT d'ULMAIRE SGLP™. *Spiraea ulmaria* extract obtained from the flower can be purchased from Indena S.A. (France) under the trade name SWEET SUPEXTRAT™ or from Greentech S.A. (France) under the trade names PHYTELENE COMPLEX EGX 250™, PHYTELENE OF QUEEN MEADOW EG 213 LIQUID™, and PHYTELENE OF ULMAIRE EG 213 LIQUID™ and SLIMMING™. *Spiraea ulmaria* extract obtained from the root can purchased from Active Organics (USA) under the trade names ACTIPHYTE OF MEADOWSWEET PG50™, CO ACTIPHYTE OF MEADOWSWEET AJ™, CO ACTIPHYTE OF MEADOWSWEET AL™, CO ACTIPHYTE OF MEADOWSWEET GL™, CO ACTIPHYTE OF MEADOWSWEET LIPO O™, CO ACTIPHYTE OF MEADOWSWEET LIPO RS™, CO ACTIPHYTE OF MEADOWSWEET LIPO S™, and CO ACTIPHYTE OF MEADOWSWEET LIPO SUN™

3. Normal Skin

The addition of *Plumeria alba* flower extract, *Euterpe oleraceae* fruit extract, and *Camellia sinensis* leaf extract to the *Silybum marianum* and gorgonian extracts was found to work well on normal skin. *Plumeria alba* flower extract is described above.

*Euterpe oleracea* (acai) is a plant that is native to Brazil. It produces dark purple fruit. Extract from the fruit of acai can be purchased from Southern Cross Botanicals Pty Ltd (NSW Australia), Amax NutraSource (USA) under the trade name ACAI FRUIT EXTRACT™, from Assessa-Industria (Brazil) under the trade name FRULIX TF ACAI™, or from Centroflora Group Botucatu (Brazil) under the trade name ACAI BERRY EXTRACT™.

*Camellia sinensis* With respect to *Camellia sinensis* extract, the *Camellia sinensis* plant is native to China, and is a flowing plant. The extract can be obtained from the whole plant or parts of said plant. In particular instances, it is from the leaf, root, flower, or seed of said extract and in particular, the leaf. In particular instances the *Camellia sinensis* extract can include a polyphenol compound such as epigallocatechin gallate. *Camellia sinensis* extract, whether from the whole plant or parts of said plant, is commercially available from a wide range of sources (see, e.g., CTFA, Volume 1, pages 400-07, which is incorporated by reference).

D. Combination of *Silybum marianum*, Luo Han Guo Fruit, and Gorgonian Extracts

Descriptions of *Silybum marianum*, luo han guo, and gorgonian extracts are described above.

Data suggests that the combination of these ingredients in a topical skin formulation can be used to treat a wide variety of skin conditions by reducing in skin cells the following: CGRP expression; Cyclo-oxygenase 1 and 2 activity; FAAH activity; lipoxygenase activity; TNF-α expression; IL-2, 8, and 10 expression; angiogenin expression; INF-γ expression; IL 12p40 expression; and tyrosinase activity. This combination also has anti-oxidative properties, which can be used to prevent or at the very least reduce oxidative damage to skin cells. This combination also can increase ICAM-1 expression in skin cells. Example 2 provides a more detailed account of these data.

E. Combination of Flax Seed and Hydrolyzed Algin Extracts

Descriptions of flax seed and hydrolyzed algin extracts are described above.

Data suggests that the combination of these ingredients in a topical skin formulation can be used to treat a wide variety of skin conditions by reducing in skin cells the following: MMP 2, 3, and 9 activity; CGRP expression; TNF-α expression; IL 6, 8, and 10 expression; IL12p40 expression, and melanogenesis activity. Further, this combination also has the ability to increase laminin production in skin cells and also to act as an involucrin reporter. Example 2 provides a more detailed account of these data.

F. Combination of Frangipani Flower and *Nymphaea gigantea* Flower Extracts

Descriptions of frangipani flower and water lily extracts are described above.

Data suggests that the combination of these ingredients in a topical skin formulation can be used to treat a wide variety of skin conditions by reducing in skin cells TNF-α expression. Further, this combination also has anti-oxidative properties and has the ability to increase collagen production in skin cells. Example 2 provides a more detailed account of these data.

G. Combination of Guava Fruit and Kanuka Leaf Extracts

Descriptions of guava fruit and kanuka leaf extracts are described above.

Data suggests that the combination of these ingredients in a topical skin formulation can be used to treat a wide variety of skin conditions by reducing in skin cells TNF-α expression and reducing elastase activity. Further, this combination also has anti-oxidative properties and has the ability to increase collagen production in skin cells. Example 2 provides a more detailed account of these data.

H. Determining Skin-Type

The primary skin types of humans are normal skin, dry skin, oily skin, and combination skin. Normal skin typically has an even tone, soft, a smooth texture, with no visible pores or blemishes, and no greasy patches or flaky areas. Therefore, a product that can retain skin moisture in its present form can be used to maintain the appearance of normal skin.

Dry skin usually has a low level of sebum and can be prone to irritation. The appearance of dry skin is usually a parched look caused by the skin's inability to retain moisture. Oftentimes it feels "tight" and uncomfortable after washing and is prone to chapping, flaking, and cracking. Dry skin can be exacerbated by wind, extremes of temperature and air-conditioning, all of which cause the skin to flake, chap and feel tight. Dry skin typically has a dull appearance. Therefore, a product that deliver appropriate hydration and restore moisture to dry skin can be used to counteract the effects of dry skin.

Oily skin is typically shiny, thick and dull colored. It typically feels oily and has coarse pores and pimples and other unsightly blemishes. Oily skin usually has oil producing sebaceous glands that are overactive and produce more oil than is needed. The oil oozes and gives the skin a greasy shine. The pores are enlarged and the skin has a coarse look. Therefore, a product that can help control skin surface oiliness while also cleansing clogged pores can be used to counteract the effects of oily skin.

Combination skin is a combination of both oily and dry skin. Usually, there is a greasy center panel consisting of nose, forehead and chin (also known as the "T-zone" of a person's face) and a dry panel consisting of cheeks, mouth and the areas around the eyes. Therefore, a product that can help control the excess oil production in sebaceous glands in the T-zone while also hydrating the dry skin areas outside of the T-zone can be used.

I. Compositions of the Present Invention

It is contemplated that the compositions of the present invention can include any amount of the ingredients. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

J. Vehicles

The compositions of the present invention can be incorporated into all types of vehicles. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

K. Cosmetic Products and Articles of Manufacture

The composition of the present invention can also be used in many cosmetic products including, but not limited to, lip sticks, lip balms, lip glosses, sunscreen products, sunless skin tanning products, hair products, finger nail products, moisturizing creams, skin benefit creams and lotions, softeners, day lotions, gels, ointments, foundations, night creams, cleansers, toners, masks, or other known cosmetic products or applications. Additionally, the cosmetic products can be formulated as leave-on or rinse-off products. In certain aspects, the compositions of the present invention are stand-alone products.

L. Additional Ingredients

In addition to the guava fruit extract compositions of the present invention can include additional ingredients such as cosmetic ingredients and pharmaceutical active ingredients. Non-limiting examples of these additional ingredients are described in the following subsections. 1. Cosmetic Ingredients The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *Ginkgo Biloba, ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenthera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, macadamia ternifolia nut oil, maltitol, matricaria (*Chamomilla recutita*) oil, methyl glucose sesquistearate, methylsilanol PCA, mineral oil, mink oil, *Mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha Piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza Sativa*) bran oil, RNA, rosemary (*Rosmarinus Officinalis*) oil, rose oil, safflower (*Carthamus Tinctorius*) oil, sage (*Salvia Officinalis*) oil, sandalwood (*Santalum Album*) oil, serine, serum protein, sesame (*Sesamum Indicum*) oil, shea butter (*Butyrospermum Parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 1600 to 2400° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

M. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

A. Example 1 (In Vivo Data)

The combination of *Silybum marianum* extract and *Momordica grosvenori* fruit extract was found through in vivo studies on women (one week study) to be effective on skin-types of normal, dry, and oily (data not shown). The *Silybum marianum* extract was a hydroalcoholic extract and the *Momordica grosvenori* fruit extract was a hydroglycolic extract. The addition of the following combinations were found to work particularly well with certain skin-types (data not shown):

- Dry Skin: The addition of *Linum usitatissimum* seed extract and hydrolyzed algin was found to work well on dry skin. The *Linum usitatissimum* seed extract was a hydroglycolic extract and the hydrolyzed algin was obtained from *Laminaria digitata.*
- Oily Skin: The addition of *Psidium guajava* fruit extract and *Kunzea ericoides* leaf extract was found to work well on oily skin. The *Psidium guajava* fruit extract was a hydroglycolic fruit extract and the *Kunzea ericoides* leaf extract was an aqueous extract.
- Normal Skin: The addition of *Plumeria alba* flower extract and *Nymphea gigantea* flower extract was found to work well on normal skin. The *Plumeria alba* flower extract was an aqueous extract and wherein the *Nymphea gigantea* flower extract was an aqueous extract.

The combination of *Silybum marianum* extract and *Pseudopterogorgia elisabethae* extract was found through in vivo studies on women (one week study) to be effective on skin-types of normal, dry, and oily (data not shown). The *Silybum marianum* extract was a hydroalcoholic extract and the *Pseudopterogorgia elisabethae* extract was a butylene glycol extract. The addition of the following combinations were found to work particularly well with certain skin-types (data not shown):

- Dry Skin: The addition of *Linum usitatissimum* seed extract and hydrolyzed algin was found to work well on dry skin. The *Linum usitatissimum* seed extract was a hydroglycolic extract and the hydrolyzed algin was obtained from *Laminaria digitata.*
- Oily Skin: The addition of *Psidium guajava* fruit extract and *Spiraea ulmaria* extract extract was found to work well on oily skin. *Psidium guajava* fruit extract was a hydroglycolic fruit extract.
- Normal Skin: The addition of *Plumeria alba* flower extract, *Euterpe oleraceae* fruit extract, and *Camellia sinensis* leaf extract was found to work well on normal skin. The *Plumeria alba* flower extract was an aqueous extract.

B. Example 2 (In Vitro Data)

Table 1 includes data concerning the combination of *Silybum marianum* extract and luo han guo fruit extract.

TABLE 1

| Assay | *Silybum marianum* Extract* | Luo Han Guo Extract* |
|---|---|---|
| CGRP Expression | −51% | − |
| Cyclo-oxygenase 1 activity inhibition | −65% | − |
| Cyclo-oxygenase 2 activity inhibition | −59% | − |
| FAAH inhibition | −41% | − |
| Lipoxygenase activity | −30% | − |
| TNF-α expression | −50% | − |
| IL 8 expression | −26.47% | − |
| IL-2 expression | −24.34% | − |
| Angiogenin expression | −31.54% | − |
| ICAM-1 expression | +2.47% | − |
| IFN-γ expression | −43.59% | − |
| IL 10 expression | −39.84% | − |
| IL12p40 expression | −37.79% | − |
| Anti-oxidant activity (ORAC)** | +135% | − |
| Anti-oxidant activity (TEAC)** | +87% | − |
| Lipid peroxidation (cell-based) | DCRS** | − |
| Mushroom tyrosinase inhibition | −50% | − |

*PRONALEN SILYMARIN HSC from Provital S.A. (SPAIN) was used to obtain data; Luo han guo fruit extract from Carrubba Inc., Milford, Connecticut (USA) was used to obtain the data.
**ORAC activity of positive control; TEAC activity of positive control; DCRS exogenous and endogenous peroxide.

Table 2 includes data concerning the combination of *Silybum marianum* extract, luo han guo fruit extract, and gorgonian extract.

TABLE 2

| Assay | *Silybum marianum* Extract* | Luo Han Guo Extract* | Gorgonian Extract* |
|---|---|---|---|
| CGRP Expression | −51% | − | |
| Cyclo-oxygenase 1 activity inhibition | −65% | − | |
| Cyclo-oxygenase 2 activity inhibition | −59% | − | −50% |
| FAAH inhibition | −41% | − | |
| Lipoxygenase activity | −30% | − | |
| TNF-α expression | −50% | − | −81% |
| IL 8 expression | −26.47% | − | |
| IL-2 expression | −24.34% | − | |
| Angiogenin expression | −31.54% | − | |
| ICAM-1 expression | +2.47% | − | |
| IFN-γ expression | −43.59% | − | |
| IL 10 expression | −39.84% | − | |
| IL12p40 expression | −37.79% | − | |
| Anti-oxidant activity (ORAC)** | +135% | − | |
| Anti-oxidant activity (TEAC)** | +87% | − | +86% |
| Lipid peroxidation (cell-based) | DCRS** | − | |
| Mushroom tyrosinase inhibition | −50% | − | |

*PRONALEN SILYMARIN HSC from Provital S.A. (SPAIN) was used to obtain data; Luo han guo fruit extract from Carrubba Inc., Milford, Connecticut (USA) was used to obtain data; Gorgonian Extract BG from Lipo Chemicals, Inc., Paterson, New Jersey (USA) was used to obtain data.
**ORAC activity of positive control; TEAC activity of positive control; DCRS exogenous and endogenous peroxide.

Table 3 includes data concerning the combination of *Silybum marianum* extract, luo han guo fruit extract, flax seed extract, and hydrolyzed algin extract.

TABLE 3

| Assay | *Silybum marianum* Extract* | Luo Han Guo Extract* | Flax Seed Extract* | Hydrolyzed Algin Extract |
|---|---|---|---|---|
| CGRP Expression | −51% | – | – | −66% |
| Cyclo-oxygenase 1 activity | −65% | – | – | – |
| Cyclo-oxygenase 2 activity | −59% | – | – | – |
| FAAH inhibition | −41% | – | – | – |
| Lipoxygenase activity | −30% | – | – | – |
| TNF-α expression | −50% | – | – | −21% |
| IL 6 expression | – | – | – | −70% |
| IL 8 expression | −26.47% | – | – | −33% |
| IL-2 expression | −24.34% | – | – | – |
| Angiogenin expression | −31.54% | – | – | – |
| ICAM-1 expression | +2.47% | – | – | – |
| IFN-γ expression | −43.59% | – | – | – |
| IL 10 expression | −39.84% | – | – | −40% |
| IL12p40 expression | −37.79% | – | – | −32% |
| Anti-oxidant activity (ORAC)** | +135% | – | – | – |
| Anti-oxidant activity (TEAC)** | +87% | – | – | – |
| Lipid peroxidation (cell-based) | DCRS** | – | – | – |
| Mushroom tyrosinase inhibition | −50% | – | – | – |
| Involucrin reporter | – | – | ++ | – |
| Laminin ELISA | – | – | +168% | – |
| MMP2 inhibition | – | – | −27% | – |
| MMP3 inhibition | – | – | −52% | – |
| MMP9 inhibition | – | – | −15% | – |
| B16 pigmentation | – | – | – | −24.50% |

*PRONALEN SILYMARIN HSC from Provital S.A. (SPAIN) was used to obtain data; Luo han guo fruit extract from Carrubba Inc., Milford, Connecticut (USA) was used to obtain data; Flax Seed Extract from Carrubba Inc., Milford, Connecticut (USA) was used to obtain data; PHYKO AL-PF from Barnet Products Corp., Englewood Cliffs, New Jersey (USA), was used to obtain data.

**ORAC activity of positive control; TEAC activity of positive control; DCRS exogenous and endogenous peroxide.

Table 4 includes data concerning the combination of *Silybum marianum* extract, luo han guo fruit extract, frangipani flower extract, and *Nymphaea gigantea* flower extract.

TABLE 4

| Assay | *Silybum marianum* Extract* | Luo Han Guo Extract* | Frangipani Flower Extract* | *Nymphaea Gigantea* Extract |
|---|---|---|---|---|
| CGRP Expression | −51% | – | – | – |
| Cyclo-oxygenase 1 activity | −65% | – | – | – |
| Cyclo-oxygenase 2 activity | −59% | – | – | – |
| FAAH inhibition | −41% | – | – | – |
| Lipoxygenase activity | −30% | – | – | – |
| TNF-α expression | −50% | – | −89% | −60% |
| IL 8 expression | −26.47% | – | – | – |
| IL-2 expression | −24.34% | – | – | – |
| Angiogenin expression | −31.54% | – | – | – |
| ICAM-1 expression | +2.47% | – | – | – |
| IFN-γ expression | −43.59% | – | – | – |
| IL 10 expression | −39.84% | – | – | – |
| IL12p40 expression | −37.79% | – | – | – |
| Anti-oxidant activity (ORAC)** | +135% | – | +30% | +38% |
| Anti-oxidant activity (TEAC)** | +87% | – | – | – |
| Lipid peroxidation (cell-based) | DCRS** | – | – | – |

TABLE 4-continued

| Assay | *Silybum marianum* Extract* | Luo Han Guo Extract* | Frangipani Flower Extract* | *Nymphaea Gigantea* Extract |
|---|---|---|---|---|
| Mushroom tyrosinase inhibition | −50% | – | – | – |
| Collagen II ELISA | – | – | – | +43% |

*PRONALEN SILYMARIN HSC from Provital S.A. (SPAIN) was used to obtain data; Luo han guo fruit extract from Carrubba Inc., Milford, Connecticut (USA) was used to obtain data; ABACROSS FRANGIPANI FLOWER BG from Southern Cross Botanicals, New South Wales (AUSTRALIA) was used to obtain data; ABACROSS WATER LILY BG from Southern Cross Botanicals, New South Wales (AUSTRALIA) was used to obtain data.

Table 5 includes data concerning the combination of *Silybum marianum* extract, luo han guo fruit extract, guava fruit extract, and kanuka leaf extract.

TABLE 5

| Assay | *Silybum marianum* Extract* | Luo Han Guo Extract* | Guava Fruit Extract* | Kanuka Leaf Extract* |
|---|---|---|---|---|
| CGRP expression | −51% | – | – | – |
| Cyclo-oxygenase 1 activity | −65% | – | – | – |
| Cyclo-oxygenase 2 activity | −59% | – | – | – |
| FAAH inhibition | −41% | – | – | – |
| Lipoxygenase activity | −30% | – | – | – |
| TNF-α expression | −50% | – | −89% | −63% |
| IL 8 expression | −26.47% | – | – | – |
| IL-2 expression | −24.34% | – | – | – |
| Angiogenin expression | −31.54% | – | – | – |
| ICAM-1 expression | +2.47% | – | – | – |
| IFN-γ expression | −43.59% | – | – | – |
| IL 10 expression | −39.84% | – | – | – |
| IL12p40 expression | −37.79% | – | – | – |
| Anti-oxidant activity (ORAC)** | +135% | – | +30% | – |
| Anti-oxidant activity (TEAC)** | +87% | – | – | +99% |
| Lipid peroxidation (cell-based) | DCRS** | – | – | – |
| Mushroom tyrosinase inhibition | −50% | – | – | – |
| Collagen II ELISA | – | – | – | +78% |
| Elastase inhibition | – | – | – | −35% |

*PRONALEN SILYMARIN HSC from Provital S.A. (SPAIN) was used to obtain data; Luo han guo fruit extract from Carrubba Inc., Milford, Connecticut (USA) was used to obtain data; Guava Fruit Extract from Carrubba Inc., Milford, Connecticut (USA) was used to obtain data; ABACROSS KANUKA BG from Southern Cross Botanicals, New South Wales (AUSTRALIA) was used to obtain data.

Table 6 includes data concerning the combination of flax seed and hydrolyzed algin extracts.

TABLE 6

| Assay | Flax Seed Extract* | Hydrolyzed Algin Extract* |
|---|---|---|
| Involucrin reporter | ++ | – |
| Laminin ELISA | +168% | – |
| MMP2 inhibition | −27% | – |
| MMP3 inhibition | −52% | – |
| MMP9 inhibition | −15% | – |
| CGRP expression | – | −66% |
| TNF-α expression | – | −21% |
| IL-6 expression | – | −70% |
| IL-8 expression | – | −33% |
| IL-10 expression | – | −40% |
| IL12p40 expression | – | −32% |
| B16 pigmentation | – | −24.50% |

*Flax Seed Extract from Carrubba Inc., Milford, Connecticut (USA) was used to obtain data;PHYKO AL-PF from Barnet Products Corp., Englewood Cliffs, New Jersey (USA), was used to obtain data.

Table 7 includes data concerning the combination of frangipani flower and *Nymphaea gigantea* flower extracts.

TABLE 7

| Assay | Frangipani Flower Extract* | *Nymphaea gigantea* Flower Extract* |
|---|---|---|
| TNF-α expression | −89% | −60% |
| Anti-Oxidant Capacity (ORAC)** | +30% | +38% |
| Collagen I ELISA | − | +43% |

*ABACROSS FRANGIPANI FLOWER BG from Southern Cross Botanicals, New South Wales (Australia) was used to obtain data; ABACROSS WATER LILY BG from Southern Cross Botanicals, New South Wales (Austmlia) was used to obtain data.
**ORAC activity of positive control.

Table 8 includes data concerning the combination of guava fruit extract and kanuka leaf extract.

TABLE 8

| Assay | Guava Fruit Extract * | Kanuka Leaf Extract* |
|---|---|---|
| TNF-α expression | − | −63% |
| Anti-Oxidant Capacity (TEAC)** | − | +99% |
| Collagen I ELISA | − | +78% |
| Elastase inhibition | − | −35% |

*Guava Fruit Extract from Carrubba Inc., Milford, Connecticut (USA) was used to obtain data; ABACROSS KANUKA BG from Southern Cross Botanicals, New South Wales (AUSTRALIA) was used to obtain data.

C. Example 3 (Formulations)

The Tables 9-19 compositions are non-limiting compositions that can be used in the context of the present invention.

TABLE 9*

| Ingredient | % Concentration (by weight) |
|---|---|
| Phase A | |
| Water | q.s |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Extract(s)** | 2.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**Extracts refers to the extracts and combinations of extracts described in Examples 1-8 and throughout the specification.

TABLE 10*

| Ingredient | % Concentration (by weight) |
|---|---|
| Phase A | |
| Water | q.s |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Extract(s)** | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.
**Extracts refers to the extracts and combinations of extracts described in Examples 1-8 and throughout the specification.

TABLE 11*

| Ingredient | % Concentration (by weight) |
|---|---|
| Water** | q.s. |
| Petrolatum | 4-6 |
| Glycerin | 2-4 |
| Glyceryl Stearate | 2-4 |
| PEG-6 Caprylic/Capric Glycerides | 2-4 |
| Shea Butter | 2-4 |
| Cetyl Alcohol | 1-2 |
| Stearyl Alcohol | 0.5 to 2 |
| Extract(s)*** | 0.001-5 |

*Formulation can be prepared by mixing the ingredients in a beaker under heat 70-75° C. until homogenous. Subsequently, the formulation can be cooled to standing room temperature (20-25° C.).
**70-80% w/w of water works well.
***Extracts refers to the extracts and combinations of extracts described throughout this specification can be used. In particular, any of the combinations discussed in Example 1 can be used to create products for all skin or for dry skin or for oily skin or for normal skin or for combination skin. Also, the 0.001-5% references the total amount of said extracts or the amount of each extract individually in the formulation.

TABLE 12*

| Ingredient | % Concentration (by weight) |
|---|---|
| Water** | q.s. |
| Sunflower seed oil | 7-10 |
| Glycerin | 3-7 |
| Cetearyl ethylhexanoate | 3-5 |
| Dicaprylyl carbonate | 1-3 |
| Glyceryl isostearate | 1-3 |
| Glyceryl stearate | 1-3 |
| PEG-8 | 0.5-2 |
| Stearic acid | 0.5-2 |
| Extract(s)*** | 0.001-5 |

*Formulation can be prepared by mixing the ingredients in a beaker under heat 70-75° C. until homogenous. Subsequently, the formulation can be cooled to standing room temperature (20-25° C.).
**70-80% w/w of water works well.
***Extracts refers to the extracts and combinations of extracts described throughout this specification can be used. In particular, any of the combinations discussed in Example 1 can be used to create products for all skin or for dry skin or for oily skin or for normal skin or for combination skin. Also, the 0.001-5% references the total amount of said extracts or the amount of each extract individually in the formulation.

TABLE 13*

| Ingredient | % Concentration (by weight) |
|---|---|
| Water** | q.s. |
| TEA-Lauryl Sulfate | 7-10 |
| Glycerin | 2-5 |
| Propylene glycol | 1-3 |
| Cocamidopropyl betaine | 1-3 |
| Sodium methyl cocoyl taurate | 1-3 |

TABLE 13*-continued

| Ingredient | % Concentration (by weight) |
|---|---|
| Dimethicone | 0.5-2 |
| Extract(s)*** | 0.001-5 |

*Formulation can be prepared by mixing the ingredients in a beaker under heat 70-75° C. until homogenous. Subsequently, the formulation can be cooled to standing room temperature (20-25° C.).
**70-80% w/w of water works well.
***Extracts refers to the extracts and combinations of extracts described throughout this specification can be used. In particular, any of the combinations discussed in Example 1 can be used to create products for all skin or for dry skin or for oily skin or for normal skin or for combination skin. Also, the 0.001-5% references the total amount of said extracts or the amount of each extract individually in the formulation.

TABLE 14*

| Ingredient | % Concentration (by weight) |
|---|---|
| Water** | q.s. |
| Butylene glycol | 5-10 |
| Glycerin | 3-7 |
| PEG-32 | 3-7 |
| Extract(s)*** | 0.001-5 |

*Formulation can be prepared by mixing the ingredients in a beaker under heat 70-75° C. until homogenous. Subsequently, the formulation can be cooled to standing room temperature (20-25° C.).
**75-85% w/w of water works well.
***Extracts refers to the extracts and combinations of extracts described throughout this specification can be used. In particular, any of the combinations discussed in Example 1 can be used to create products for all skin or for dry skin or for oily skin or for normal skin or for combination skin. Also, the 0.001-5% references the total amount of said extracts or the amount of each extract individually in the formulation.

TABLE 15*

| Ingredient | % Concentration (by weight) |
|---|---|
| Water** | q.s. |
| Butylene glycol | 3-5 |
| Glycerin | 3-5 |
| PEG-32 | 3-5 |
| Extract(s)*** | 0.001-5 |

*Formulation can be prepared by mixing the ingredients in a beaker under heat 70-75° C. until homogenous. Subsequently, the formulation can be cooled to standing room temperature (20-25° C.).
**80-90% w/w of water works well.
***Extracts refers to the extracts and combinations of extracts described throughout this specification can be used. In particular, any of the combinations discussed in Example 1 can be used to create products for all skin or for dry skin or for oily skin or for normal skin or for combination skin. Also, the 0.001-5% references the total amount of said extracts or the amount of each extract individually in the formulation.

TABLE 16*

| Ingredient | % Concentration (by weight) |
|---|---|
| Water** | q.s. |
| Butylene glycol | 1-3 |
| Glycerin | 1-3 |
| Extract(s)*** | 0.001-5 |

*Formulation can be prepared by mixing the ingredients in a beaker under heat 70-75° C. until homogenous. Subsequently, the formulation can be cooled to standing room temperature (20-25° C.).
**90-96% w/w of water works well.
***Extracts refers to the extracts and combinations of extracts described throughout this specification can be used. In particular, any of the combinations discussed in Example 1 can be used to create products for all skin or for dry skin or for oily skin or for normal skin or for combination skin. Also, the 0.001-5% references the total amount of said extracts or the amount of each extract individually in the formulation.

TABLE 17*

| Ingredient | % Concentration (by weight) |
|---|---|
| Water** | q.s. |
| Cetearyl ethylhexanoate | 5-10 |
| Glycerin | 3-7 |
| Caprylic/Capric triglyceride | 3-5 |
| Butylene glycol | 2-5 |
| Sunflower Seed Oil | 2-5 |
| Glyceryl Stearate | 1-3 |
| Isostearyl alcohol | 1-3 |
| Petrolatum | 1-3 |
| Stearic Acid | 0.5-2 |
| Betaine | 0.5-2 |
| Extract(s)*** | 0.001-5 |

*Formulation can be prepared by mixing the ingredients in a beaker under heat 70-75° C. until homogenous. Subsequently, the formulation can be cooled to standing room temperature (20-25° C.).
**60-70% w/w of water works well.
***Extracts refers to the extracts and combinations of extracts described throughout this specification can be used. In particular, any of the combinations discussed in Example 1 can be used to create products for all skin or for dry skin or for oily skin or for normal skin or for combination skin. Also, the 0.001-5% references the total amount of said extracts or the amount of each extract individually in the formulation.

TABLE 18*

| Ingredient | % Concentration (by weight) |
|---|---|
| Water** | q.s. |
| Glycerin | 3-7 |
| Butylene glycol | 3-5 |
| Cetearyl Ethylhexanoate | 3-5 |
| Caprylic/Capric triglyceride | 1-3 |
| Glyceryl Stearate | 1-3 |
| Dimethicone | 1-3 |
| Betaine | 0.5-2 |
| Isostearyl alcohol | 0.5-2 |
| Stearic acid | 0.5-2 |
| Extract(s)** | 0.001-5 |

*Formulation can be prepared by mixing the ingredients in a beaker under heat 70-75° C. until homogenous. Subsequently, the formulation can be cooled to standing room temperature (20-25° C.).
**70-80% w/w of water works well.
***Extracts refers to the extracts and combinations of extracts described throughout this specification can be used. In particular, any of the combinations discussed in Example 1 can be used to create products for all skin or for dry skin or for oily skin or for normal skin or for combination skin. Also, the 0.001-5% references the total amount of said extracts or the amount of each extract individually in the formulation.

TABLE 19*

| Ingredient | % Concentration (by weight) |
|---|---|
| Water** | q.s. |
| Glycerin | 3-5 |
| Isododecane | 3-5 |
| Butylene glycol | 3-5 |
| Dimethicone | 1-3 |
| Betaine | 0.5-2 |
| Extract(s)*** | 0.001-5 |

*Formulation can be prepared by mixing the ingredients in a beaker under heat 70-75° C. until homogenous. Subsequently, the formulation can be cooled to standing room temperature (20-25° C.).
**75-85% w/w of water works well.
***Extracts refers to the extracts and combinations of extracts described throughout this specification can be used. In particular, any of the combinations discussed in Example 1 can be used to create products for all skin or for dry skin or for oily skin or for normal skin or for combination skin. Also, the 0.001-5% references the total amount of said extracts or the amount of each extract individually in the formulation.

D. Example 4 (Assays Used to Obtain Data)

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, cultivated in standard DMEM growth medium with 10% fetal bovine serum (Mediatech) at 37° C. in 10% $CO_2$, were treated with each of the extracts identified in Tables 1-8 for 6 days. Following incubation, melanin secretion was measured by absorbance at 405 nm and cellular viability was quantified.

Collagen Stimulation Assay: Collagen is an extracellular matrix protein critical for skin structure. Increased synthesis of collagen helps improve skin firmness and elasticity. This bioassay analyzes the effect of extracts on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples are pipetted into the wells and any procollagen peptide □present is bound by the immobilized antibody. After washing away any unbound substances, an enzyme-linked polyclonal antibody specific for procollagen peptide is added to the wells. Following a wash to remove any unbound antibody-enzyme reagent, a substrate solution is added to the wells and color develops in proportion to the amount of procollagen peptide bound in the initial step using a microplate reader for detection at 450 nm. The color development is stopped and the intensity of the color is measured. Subconfluent normal human adult epidermal fibroblasts (Cascade Biologics) cultivated in standard DMEM growth medium with 10% fetal bovine serum (Mediatech) at 37° C. in 10% $CO_2$, were treated with each of the extracts identified in Tables 1-8 for 3 days. Following incubation, cell culture medium was collected and the amount of procollagen peptide secretion quantified using a sandwich enzyme linked immuno-sorbant assay (ELISA) from Takara (#MK101).

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay analyzes the effect of extracts on the production of TNF-α by human epidermal keratinocytes. The endpoint of this assay is a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples are pipetted into the wells and any TNF-α □present is bound by the immobilized antibody. After washing away any unbound substances, an enzyme-linked polyclonal antibody specific for TNF-α is added to the wells. Following a wash to remove any unbound antibody-enzyme reagent, a substrate solution is added to the wells and color develops in proportion to the amount of TNF-α bound in the initial step using a microplate reader for detection at 450 nm. The color development is stopped and the intensity of the color is measured. Subconfluent normal human adult keratinocytes (Cascade Biologics) cultivated in EpiLife standard growth medium (Cascade Biologics) at 37° C. in 5% $CO_2$, were treated with phorbol 12-myristate 13-acetate (PMA, 10 ng/ml, Sigma Chemical, #P1585-1MG) and each of the extracts identified in Tables 1-8 for 6 hours. PMA has been shown to cause a dramatic increase in TNF-α secretion which peaks at 6 hours after treatment. Following incubation, cell culture medium was collected and the amount of TNF-α secretion quantified using a sandwich enzyme linked immuno-sorbant assay (ELISA) from R&D Systems (#DTA00C).

Antioxidant (AO) assay: An in vitro bioassay that measures the total anti-oxidant capacity of an extract. The assay relies on the ability of antioxidants in the sample to inhibit the oxidation of ABTS® (2,2'-azino-di-[3-ethylbenzthiazoline sulphonate]) to ABTS®·+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Michigan USA) was used as an in vitro bioassay to measure the total anti-oxidant capacity of each of the extracts identified in Tables 1-8. The protocol was followed according to manufacturer recommendations. The assay relied on antioxidants in the sample to inhibit the oxidation of ABTS® (2,2'-azino-di-[3-ethylbenzthiazoline sulphonate]) to ABTS®·+ by metmyoglobin. The capacity of the antioxidants in the sample to prevent ABTS oxidation was compared with that Trolox, a water-soluble tocopherol analogue, and was quantified as a molar Trolox equivalent.

ORAC Assay: Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH. The extracts identified in Tables 1-8 were subjected to this assay.

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) was incubated with its substrate L-Dopa (Fisher) in the presence or absence of each of the extracts in Tables 1-8. Pigment formation was evaluated by colorimetric plate reading at 490 nm. The percent inhibition of mushroom tyrosinase activity was calculated compared to non-treated controls to determine the ability of test extracts to inhibit the activity of purified enzyme. Test extract inhibition was compared with that of kojic acid (Sigma).

Matrix Metalloproteinase Enzyme Activity (MMP3; MMP9) Assay: An in vitro matrix metalloprotease (MMP)

inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm (ε=13,600 M-lcm-1 at pH 6.0 and above 7). The extracts identified in Tables 1-8 were subjected to this assay.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical), was used to analyze the effects of each of the extracts identified in Tables 1-8 on the activity of purified cyclooxygenase enzyme (COX-1 or COX-2). According to manufacturer instructions, purified enzyme, heme and test extracts were mixed in assay buffer and incubated with shaking for 15 min at room temperature. Following incubation, arachidonic acid and colorimetric substrate were added to initiate the reaction. Color progression was evaluated by colorimetric plate reading at 590 nm. The percent inhibition of COX-1 or COX-2 activity was calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) was used to determine the ability of each of the extracts identified in Tables 1-8 to inhibit enzyme activity. Purified 15-lipoxygenase and test extracts were mixed in assay buffer and incubated with shaking for 10 min at room temperature. Following incubation, arachidonic acid was added to initiate the reaction and mixtures incubated for an additional 10 min at room temperature. Colorimetric substrate was added to terminate catalysis and color progression was evaluated by fluorescence plate reading at 490 nm. The percent inhibition of lipoxygenase activity was calculated compared to non-treated controls to determine the ability of test extracts to inhibit the activity of purified enzyme.

Elastase Assay: EnzChek® Elastase Assay (Kit #E-12056) from Molecular Probes (Eugene, Oregon USA) was used as an in vitro enzyme inhibition assay for measuring inhibition of elastase activity for each of the extracts identified in Tables 1-8. The EnzChek kit contains soluble bovine neck ligament elastin that has been labeled with dye such that the conjugate's fluorescence is quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at −505 nm and fluorescence emission maxima at −515 nm. The peptide, chloromethyl ketone, is used as a selective, collective inhibitor of elastase when utilizing the EnzChek Elastase Assay Kit for screening for elastase inhibitors.

E. Example 5 (Additional Assays)

Additional assays that can be used to determine the efficacy of any one of the compositions disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. A composition of the present invention can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method for reducing inflammation, soothing irritated skin, or reducing inflammation and soothing irritated skin of a subject in need thereof, the method comprising topically applying to the skin of the subject a sufficient amount of a composition to reduce inflammation, sooth irritated skin, or reduce inflammation and sooth irritated skin, wherein the composition comprises *Linum usitatissimum* seed extract and hydrolyzed algin, and wherein the composition reduce inflammation, sooths irritated skin, or reduces inflammation and sooths irritated skin.

2. The method of claim 1, wherein the composition reduces TNF-alpha expression in the skin.

3. The method of claim 1, wherein the composition is a gel or a serum.

4. The method of claim 1, wherein the composition is an emulsion.

5. The method of claim 4, wherein the emulsion is an oil-in-water emulsion.

6. The method of claim 1, wherein the composition is a facial cleanser.

7. The method of claim 1, wherein the composition is applied to a fine line or wrinkle and reduces the appearance of the fine line or wrinkle.

8. The method of claim 1, wherein the composition reduces erythema.

9. The method of claim 1, wherein the composition is applied to dry skin.

10. The method of claim 1, wherein the composition moisturizes skin.

11. The method of claim 1, wherein the *Linum usitatissimum* seed extract is a hydroglycolic extract.

12. The method of claim 1, wherein the composition comprises 0.0001 to 5% by weight of the *Linum usitatissimum* seed extract.

13. The method of claim 1, wherein the composition further comprises:

glycerin;

cetyl alcohol; and xanthan gum.

14. The method of claim 1, wherein the composition further comprises one or more of:

butylene glycol;

ascorbyl palmitate;

*Borago officinalis* extract;

caprylic/capric triglyceride;

disodium EDTA;

*Elaeis guineensis* (palm) oil;

hydrogenated lecithin;

lecithin;

mannitol;

retinyl palmitate;

*sclerotium* gum; and tocopheryl acetate.

15. A serum or cleanser composition comprising:

*Linum usitatissimum* seed extract;

hydrolyzed algin;

glycerin;

cetyl alcohol; and xanthan gum, wherein the composition comprises a sufficient amount of *Linum usitatissimum* seed extract and hydrolyzed algin to reduce inflammation, sooth irritated skin, or reduce inflammation and sooth irritated skin.

16. The composition of claim 15, wherein the composition is a serum.

17. The composition of claim 15, wherein the composition is a cleanser.

18. The composition of claim 15, wherein the composition is an emulsion.

19. The composition of claim 18, wherein the emulsion is an oil-in-water emulsion.

* * * * *